United States Patent

Haddad et al.

[11] 4,033,825
[45] * July 5, 1977

[54] CELL CULTURE SYSTEM

[75] Inventors: Ihsan A. Haddad, Bedford; Alvin R. Arsenault, Burlington, both of Mass.

[73] Assignee: Instrumentation Laboratory, Inc., Lexington, Mass.

[ * ] Notice: The portion of the term of this patent subsequent to June 3, 1992, has been disclaimed.

[22] Filed: Feb. 6, 1975

[21] Appl. No.: 547,703

Related U.S. Application Data

[63] Continuation of Ser. No. 365,535, May 31, 1973, Pat. No. 3,887,436.

[52] U.S. Cl. .................. 195/127; 195/140; 195/142
[51] Int. Cl.[2] ........................................ C12K 9/00
[58] Field of Search .......... 195/127, 139, 140, 142, 195/143

[56] References Cited

UNITED STATES PATENTS

| | | | |
|---|---|---|---|
| 2,975,553 | 3/1961 | Paul | 195/143 |
| 3,732,149 | 5/1973 | Santero | 195/127 |
| 3,827,943 | 8/1974 | Mann | 195/127 |
| 3,873,423 | 3/1975 | Munder et al. | 195/127 |
| 3,887,436 | 6/1975 | Haddad et al. | 195/127 |
| 3,941,662 | 3/1976 | Munder | 195/127 |

Primary Examiner—Alvin E. Tanenholtz

[57] ABSTRACT

A cell culture system includes an incubator chamber, and a carriage that is removable from the incubator chamber and that carries a plurality of cell culture chambers. Also mounted on the carriage are a manifold structure having supply and return conduits, detachable coupling structure for connecting the cell culture chambers to the manifold structure and pump structure for circulating nutrient material between the manifold structure and the connected cell culture chambers.

12 Claims, 16 Drawing Figures

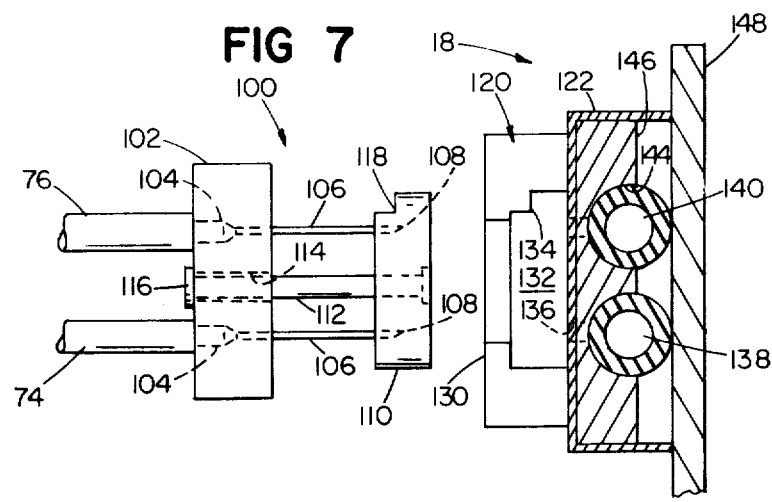
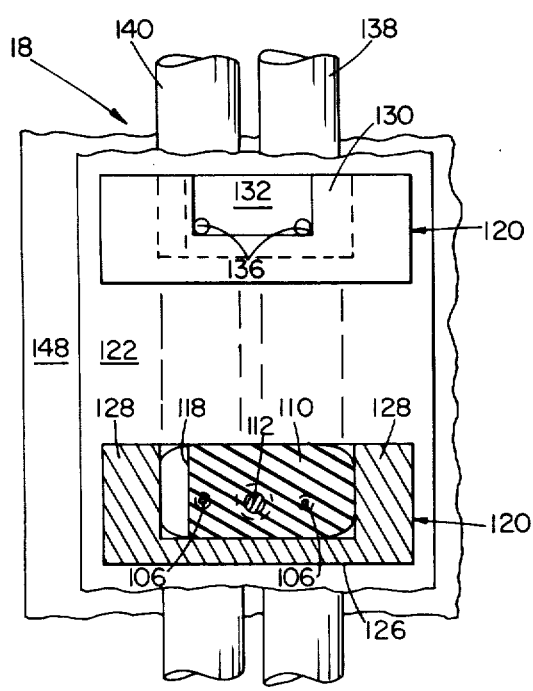
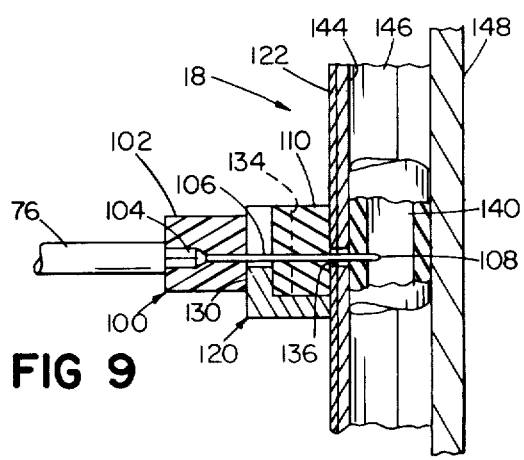

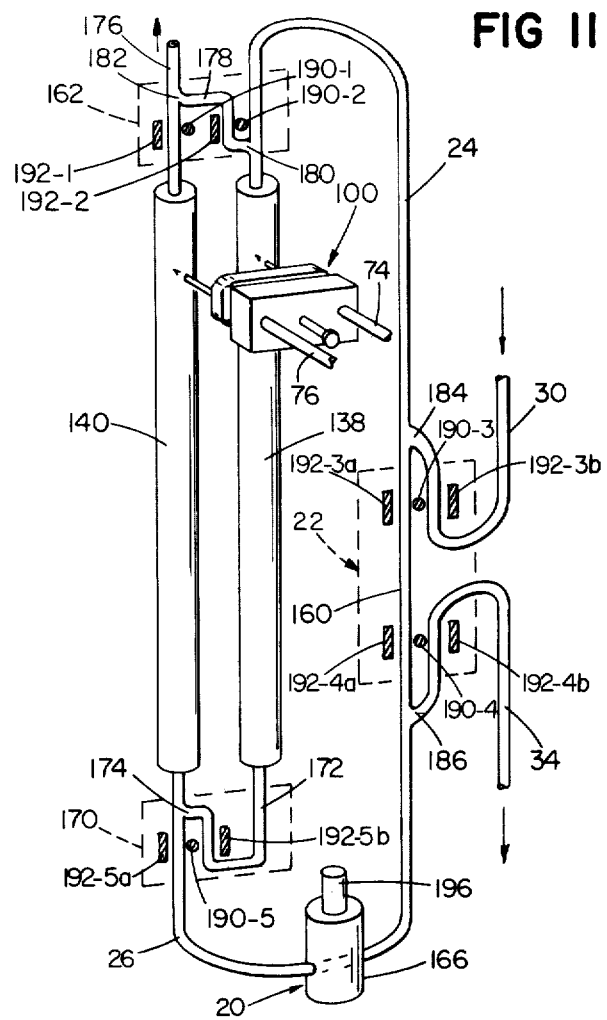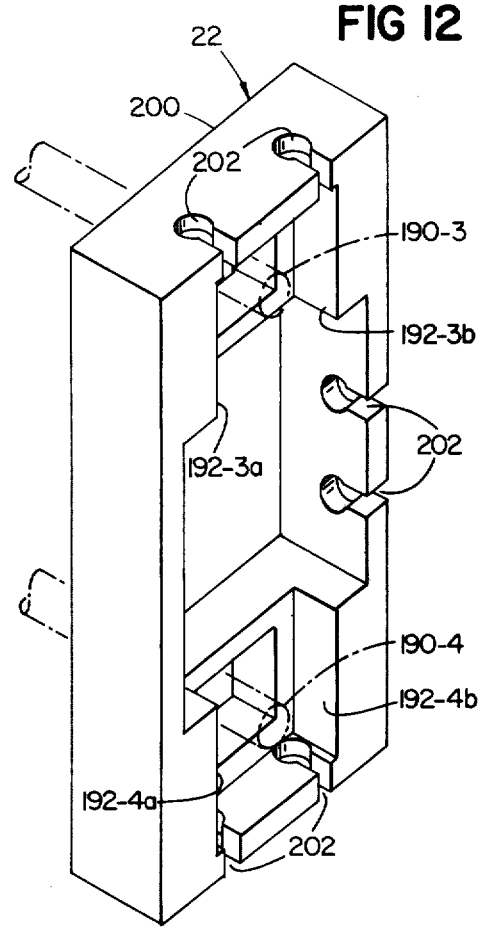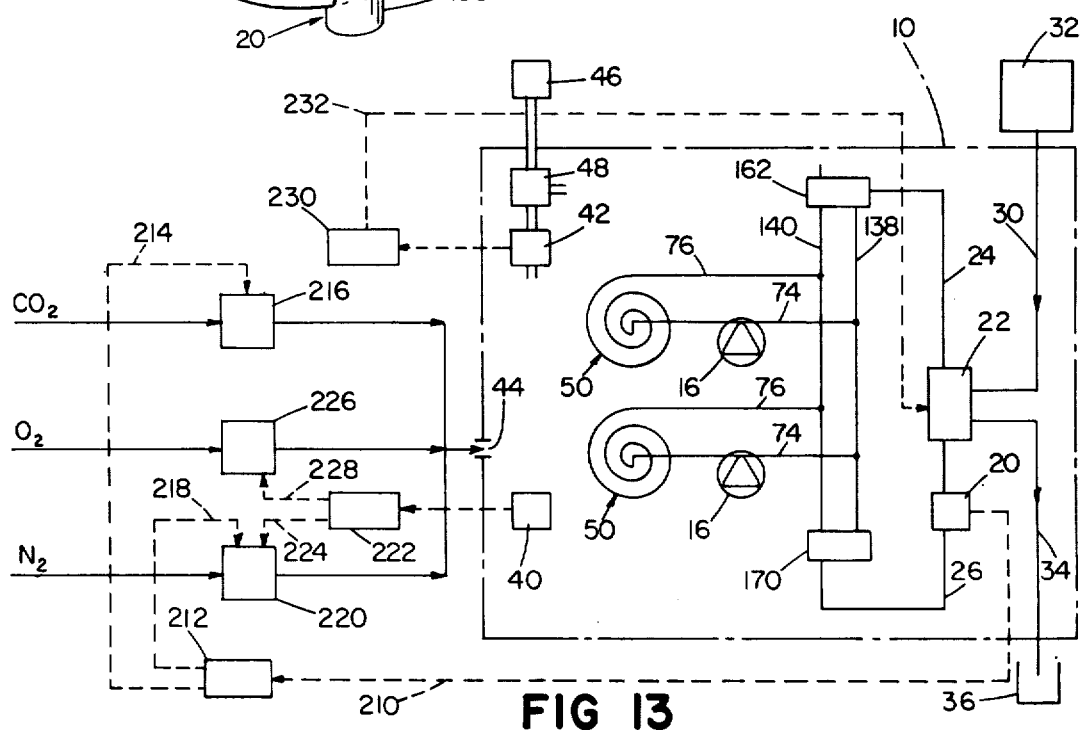

4,033,825

CELL CULTURE SYSTEM

This application is a continuation in part of our copending patent application Ser. No. 365,535, filed May 31, 1973, entitled "Fluid Handling" now U.S. Pat. No. 3,887,436.

SUMMARY OF INVENTION

This invention relates to fluid handling apparatus and more particularly to systems and apparatus particularly useful in systems for cell culture, and especially to novel and improved systems particularly adapted for large scale cell culture in which the conditions in the both liquid and gaseous phase in the culture environment are monitored to provide an environment conducive to cell growth.

Numerous cell propagation arrangements have been proposed in which conditions are established which approach the cell environment in the intact animal. An example of such a proposed system is described in the article "Cell Propagation on Films of Polymeric Fluorocarbon as a Means to Regulate Pericellular pH and $PO_2$ in Cultured Monolayers", Munder et al., FEBS Letters, Vol. 15, No. 3, June, 1971, page 191.

An object of this invention is to provide improved apparatus for the large scale culturing of cells and similar material, for example cells of animal origin. Ample supplies of cells are required for virus vaccine manufacture. Similarly, microbiologists require substantial supplies of cells, for example for cancer research and invitro growth of animal viruses. The handling of such materials, for example biological serums, nutrient media, cell cultures and other biological samples require a sterile exchange of fluids. Where the fluids are toxogenic, particular care is required in their handling. It is an object of this invention to provide novel and improved arrangements for handling biological media.

A more specific object of the invention is to provide novel and improved replaceable arrangements for use in cell culture systems.

Still further objects of the invention are to provide novel and improved arrangements for handling multiple cell culture chambers.

In accordance with one feature of the invention there is provided a replaceable, sterilizable, cell growth assembly that includes a chamber of gas permeable liquid impermeable material having an inner surface to which cells attach. The chamber is of spiral configuration and defines an elongated flow path between inlet and outlet ports. A spacer interlayer between adjacent turns of the chamber spiral maintains the adjacent turns spaced from one another to permit gas to contact surfaces of the chamber along the length of the spiral.

While the sample chamber may have a number of different configurations, in a particular embodiment the cell growth assembly includes two elongated flexible conduit tubes, one end of each tube being connected to a corresponding one of the ports and the other end of each tube is adapted for detachable connection to cooperating structure. The chamber is of steam sterilizable plastic material and has a roughened inner surface which facilitates cell attachment. Structure disposed within the inlet conduit tube cooperates with a peristaltic pump so that a length of tubing may be maintained in tension when trained about the pump cage.

In accordance with another feature of the invention there is provided a cell culture system which includes a housing, support in the housing for a cell culture substrate, the substrate being of gas permeable, liquid impermeable material and having a first surface to which cells are attachable and an opposite second surface adapted to be exposed to the gaseous environment in the housing. A circulation path includes return and supply conduits connected to the substrate and a pump is provided for circulating nutrient media along the circulation path and across the first surface of the substrate. A valve and a pH sensor are disposed in the circulation path and a carbon dioxide sensor is disposed in the housing. A first control is responsive to the pH sensor for controlling the introduction of carbon dioxide to the housing, and a second control is responsive to the carbon dioxide sensor for operating the valve to discard at least a portion of the nutrient media circulating in the system and replace such discarded portion with fresh nutrient media.

In accordance with another feature of the invention there is provided a sterilizable cell growth chamber carriage assembly that is removable as a unit from the incubator. Mounted on this carriage assembly are support for a plurality of cell culture chambers, a nutrient manifold structure having supply and return conduits, circulation path structure for circulating nutrient media between the cell culture chambers and the manifold structure and sensor structure on the carriage assembly for sensing media in the circulation path and providing an output signal representative thereof.

Components of this system in a particular embodiment are replaceable and steam sterilizable and thus provide a high degree of sterility and convenience in use in an arrangement particularly adapted for large scale cell culture.

Other objects, features and advantages of the invention will be seen as the following description of particular embodiments progresses, in conjunction with the drawings, in which:

FIG. 7 is a plan view of coupling structure of a cell culture unit and a cooperating manifold coupling, partially in section;

FIG. 8 is a view similar to FIG. 7 showing the coupling structures in a second position;

Figure 1:
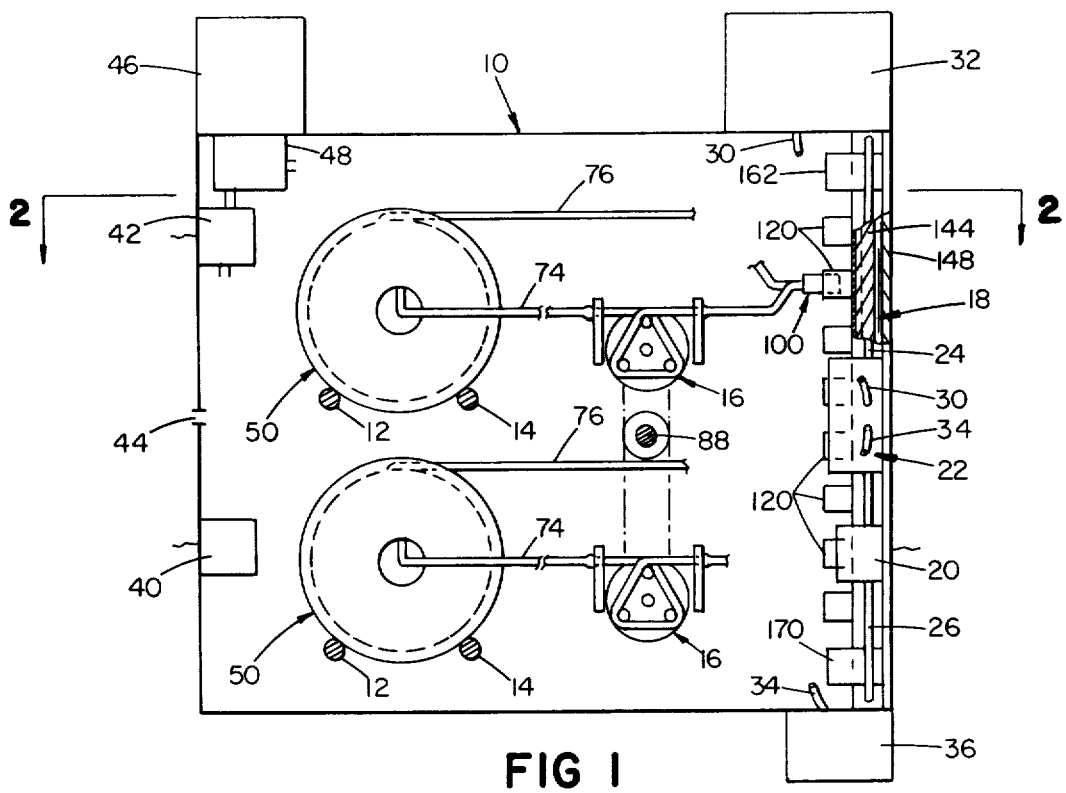
FIG. 1 is a diagrammatic side view of a cell culture system.
Figure 14:
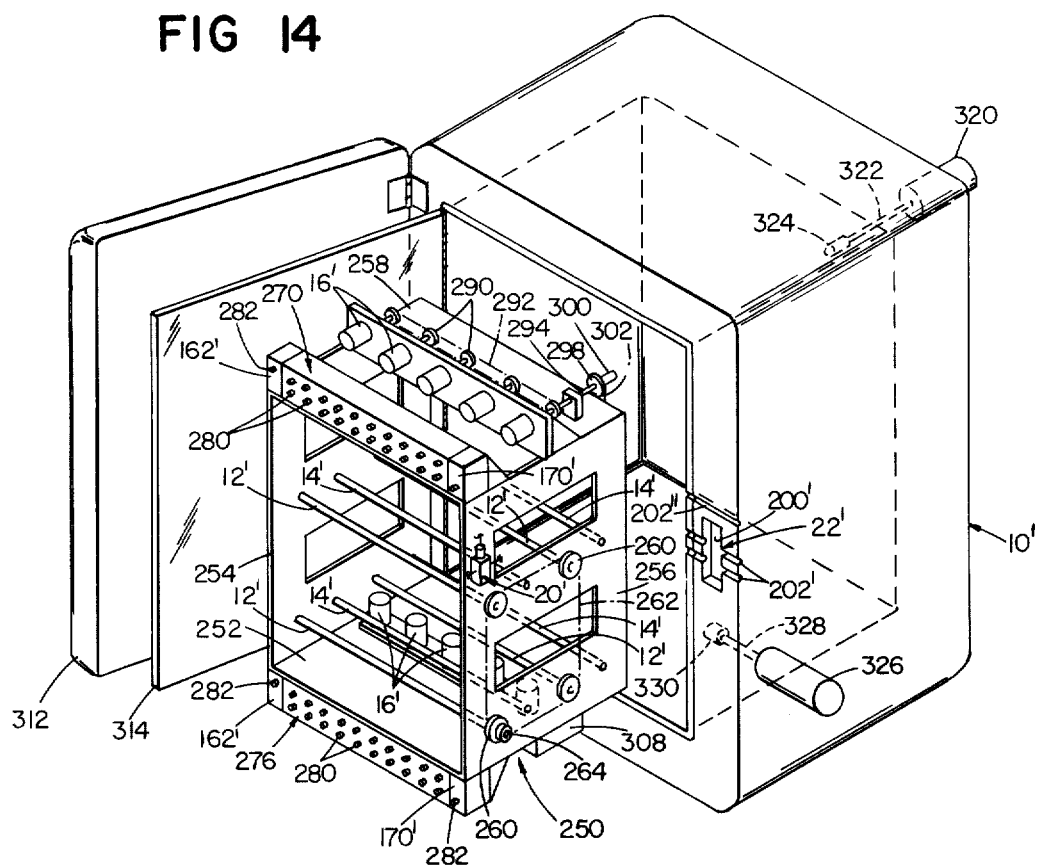
Figure 15:
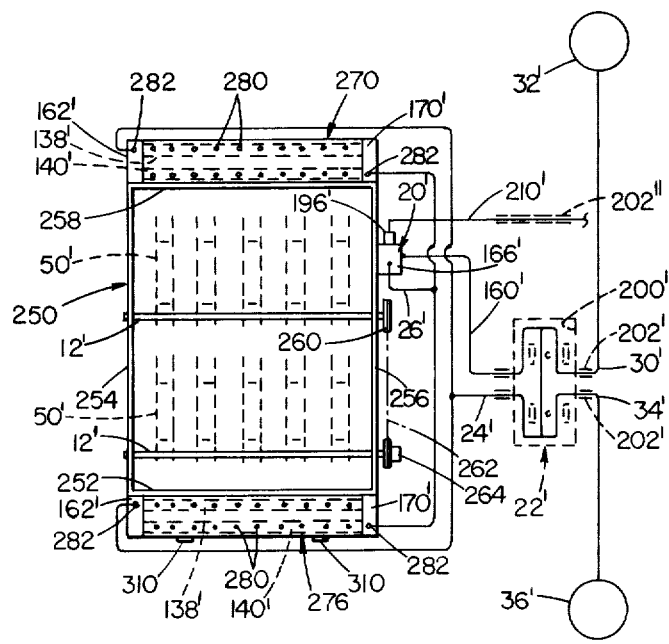
Figure 16:
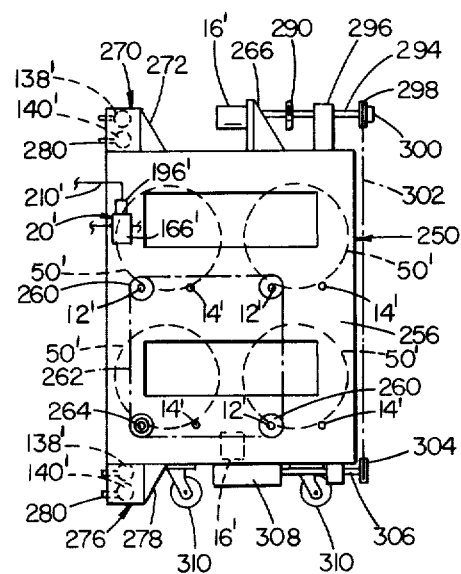

FIGS. 9 and 10 are sectional views taken along the lines 9—9 and 10—10, respectively, of the coupling structures shown in FIG. 8;

FIG. 11 is a perspective view showing features of the coupling and manifold structure and associated valving;

FIG. 12 is a perspective view of a valve housing employed in the system shown in FIG. 11;

FIG. 13 is a diagram indicating control aspects of the system shown in FIG. 1;

FIG. 14 is a perspective view of an incubator structure and removable cell chamber support assembly;

FIG. 15 is a front diagrammatic view of the removable cell chamber support assembly shown in FIG. 14; and FIG. 16 is a side diagrammatic view of the removable cell chamber support assembly shown in FIG. 14.

DESCRIPTION OF PARTICULAR EMBODIMENTS

Figure 2:
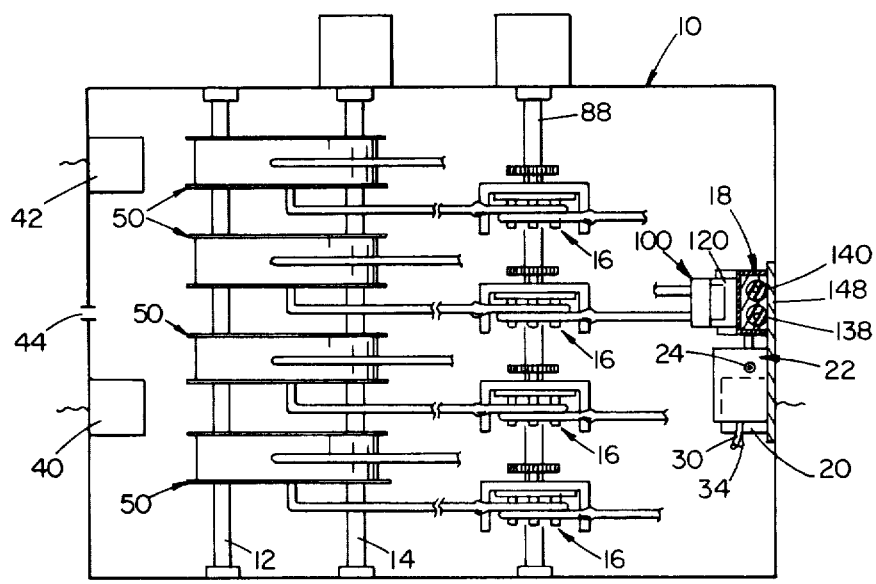
FIG. 2 is a sectional view of the system taken along the line 2—2 of FIG. 1.

With reference to FIGS. 1 and 2, there is diagrammatically shown a housing in the form of incubator 10, the interior of which is held at a precisely controlled, uniform temperature by suitable heating sources and controls in conventional manner. Disposed in incubator 10 are cell culture chamber support structure in the form of roller rod elements 12, 14, a series of peristaltic pump cages 16, and a manifold structure 18. Mounted adjacent manifold structure 18 is a pH sensing unit 20 and a valve unit 22. The valve unit 22 has, in addition to conduit 24 connected to the upper end of manifold structure 18 and conduit 26 connected via pH sensing unit 20 to the lower end of manifold structure 18, an inlet conduit 30 connected to a supply of nutrient media 32 and an outlet conduit 34 connected to collection container 36. Other sensors in the incubator chamber include oxygen sensor 40 and carbon dioxide sensor 42. Oxygen, nitrogen, and carbon dioxide are supplied through port 44 to the incubator chamber, and a source 46 of calibrating carbon dioxide is connected to sensor 42 through valve 48.

Figure 3:
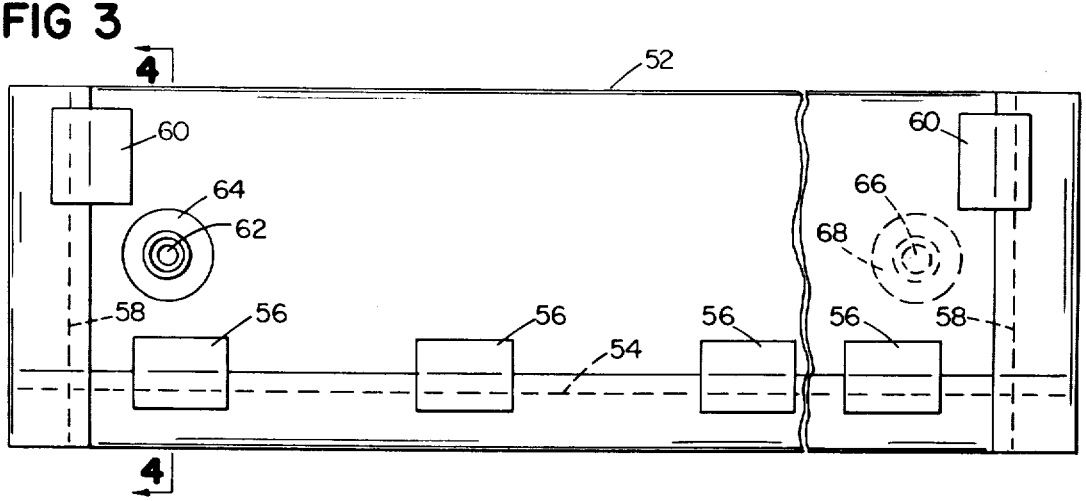
FIG. 3 is a plan view, with parts broken away, of a cell culture chamber employed in the system shown in FIG. 1.
Figure 4:
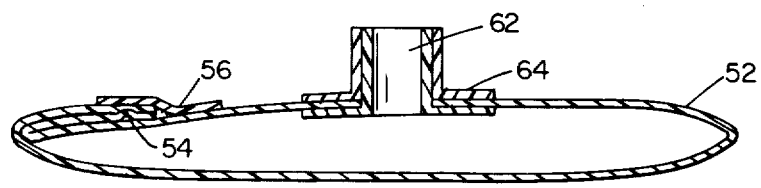
FIG. 4 is a sectional view of the culture chamber taken along the line 4—4 of FIG. 3.
Figure 5:
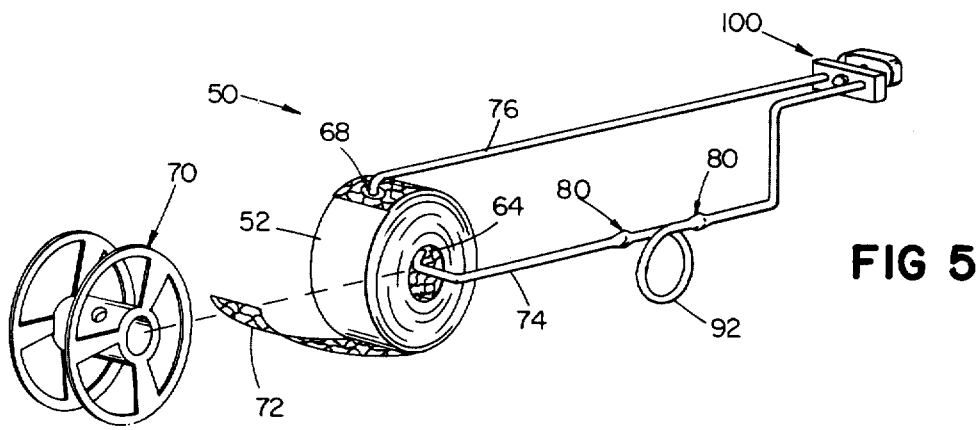
FIG. 5 is a perspective view of components of a detachable cell culture unit for use in the system shown in FIG. 1.

The system illustrated in FIGS. 1 and 2 is arranged to receive detachable cell culture units 50, additional details of which may be seen with reference to FIGS. 3–5. Each cell culture unit includes an elongated chamber 52 which in this particular embodiment has a length of twenty-four feet and a width, as viewed in FIG. 3, of 2½ inches. The chamber is made of sheet (one mil thick) of fluorinated ethylene-propylene copolymer (Teflon FEP) one surface of which has been chemically etched. The sheet has been folded in half and the two longitudinal edges heat sealed together along the line 54. The heat sealed edge is then folded over as indicated in FIG. 4 and the edge portion secured in place at intervals along the length of the chamber by adhesive tape 56. A similar seal is made at each end by heat seal 58 and secured with tape element 60. The composite seals provide a chamber that is steam sterilizable and withstands fluid pressures of flowing nutrient media. Inlet port 62 is defined by coupling 64 at one end of chamber 52 and similarly outlet port 66 is similarly defined by coupling 68. This chamber is impermeable to liquids but permeable to gases. Its chemically etched inner surface provides a surface to which cells to be cultured adhere.

Figure 6:
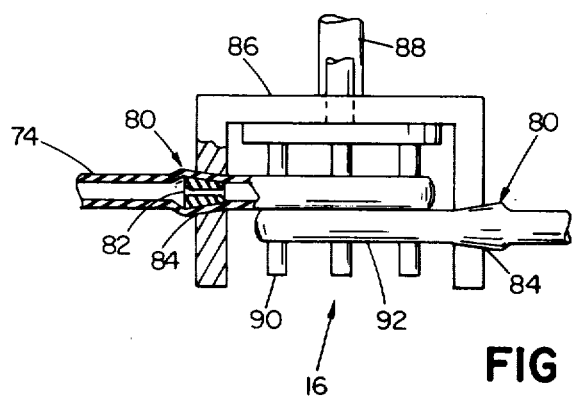
FIG. 6 is a diagrammatic view, partially in section, of peristaltic pump structure employed in the system shown in FIG. 1.

Chamber 52 is spirally wound on reel 70 (FIG. 5) with a spacer interlayer 72 that maintains the adjacent turns of the spiral spaced from one another to permit gas to contact with surfaces of the chamber 52 along the length of the spiral. Input conduit 74 is connected to inlet connector 64 and output conduit 76 is connected to outlet connector 68. Disposed in inlet conduit 74 are two tube locks 80, additional details of which may be seen with reference to FIG. 6.

Each tube lock 80 is a frustoconical member that has a bore 82, the ends of which are flared to promote smooth flow. The lock 80 expands the peristaltic tubing 74 and is adapted to cooperate with a similarly tapered aperture 84 in frame member 86 of the peristaltic pump 16 on which the drive shaft 88 for the pump cage 90 is mounted. The tube locks 80 are spaced apart in the peristaltic tubing 74 a predetermined distance so that the tube is under tension when the loop 92 is wound about the pump cage 90 and the tube locks 80 are secured in recesses 84. This arrangement provides a simple sterilizable mechanism for positively securing the tubing under tension about the pump cage 90.

Secured to the ends of conduits 74 and 76 is a coupling structure 100, additional details of which may be seen with reference to FIG. 7. The coupling 100 includes a body structure 102 which houses two connector structures 104 to which the inlet and outlet conduits 74, 76 are attached. Extending forward from each coupling structure 104 is a rigid metal conduit 106 in the form of a hypodermic needle having a sharp tip 108 and a port in the tip. The tips of the needles are encapsulated in an elastomeric (gum rubber) sealing member 110. Secured to sealing member 110 is guide shaft 112 which extends rearwardly through an aperture 114 in body member 102. Stop 116, mounted on shaft 112 limits the forward movement of that shaft and seal member 110. An interlock notch 118 may be provided for facilitating orientation of the coupling structure.

Cooperating with coupling 100 is a manifold coupling structure 120 which is mounted on the manifold structure 18. The manifold structure includes a frame member 122 on which are mounted a series of coupling structures 120 as shown in FIGS. 7 and 10. Each structure includes a base 126, two side walls 128 and a front wall 130 that define a receptacle 132 for receiving the guard member. Interlock projection 134 is adpated to cooperate with interlock notch 118. Formed in manifold frame 122 in line with each receptacle 132 are two apertures 136 which are aligned with manifold tubes 138, 140, respectively. Each tube 138, 140 is disposed in a corresponding longitudinally extending recess 144 of securing member 146 and retained in position by plate 148.

In operation of the cooperating coupling structures, the chamber coupling assembly 100 is initially sealed by the fact that the inlet and outlet orifices are disposed in and sealed by the elastomeric seal member 110. To connect a culture chamber assembly to the manifold structure 18, the seal member 110 is inserted and frictionally held in position in receptacle 132 (notch 118 cooperating with projection 134 to insure the insertion of the seal member 110 in proper orientation). After the seal member has been seated in receptacle 132, the body portion 102 is urged forward, as guided by rod 112, forcing the needle tips through the elastomeric seal material, the passageway 136 in manifold assembly and the elastomeric walls of manifold conduits 138, 140 into the position shown in FIG. 8. In that position the orifices in tips 108 are disposed in the manifold conduits 138, 140 and the culture chamber 52 is in fluid communication with the manifold conduits.

To separate the coupling structures, the body member 102 is pulled rearwardly against stop 116, withdrawing the needle tips from the manifolds 18 and placing them within the seal member 110. The elastomeric characterisitics of the conduits 138, 140 and the seal member 110 cause the punctures to immediately reseal in both the culture chamber inlet and outlet passages and the manifold conduits 138, 140.

Additional details of the manifold tubing subassembly may be seen with reference to FIG. 11. That subassembly is replaceable and includes the two elastomeric manifold tubes 138, 140 and peristaltic connecting conduits. The upper end of inlet tube 138 is connected via conduit 24 (which extends through valve 162) and tubing 160 (which extends through valve 22), and valve 22 to pH sensor cuvette 166. The other port of cuvette 166 is connected to tubing 26 which extends through valve 170 to the lower end of outlet manifold tube 140. The lower end of inlet manifold tube 138 is connected to tube 172 which extends through valve 170 and is connected to tube 168 at junction 174. The upper end of outlet manifold tube 140 is connected to relief tube 176 and a junction tube 178 extends from junction 180 with tube 160 to junction 182 with tube 176 (through valve 162). Supply tube 30 extends through valve 22 and is connected to tube 160 at junction 184 while discharge tube 34 extends through valve 22 and is connected to tube 160 at junction 186.

Each valve 22, 162 and 170 includes one or more operator rods or bars 190 which cooperate with backup surface 192 so that when the valve rod is moved towards a cooperating backup surface, it compresses the interposed peristaltic tubing to provide a seal. In valve 162, there are two valve rods 190-1 and 190-2 and two backup surfaces, rod 190-1 cooperating with backup surface 192-1 and rod 190-2 cooperating with backup surface 192-2. The rods are mounted for movement as a unit and when they are moved to the left (into their normal position), rod 190-1 closes the vent or relief 182 to the outlet manifold 140 and rod 190-2 closes via junction line 178, the relief to inlet manifold 138. When the rods are moved to the right, the relief passages to both manifolds are opened.

With reference to valve 22, that valve includes valve rod 190-3 (which cooperates with backup surfaces 192-3a and 192-3b) and valve rod 190-4 (which cooperates with backup surfaces 192-4a and 192-4b). The rods are mounted for movement as a unit and when in their right (normal) position (compressing the tubes against surfaces 192-3b and 192-4b), conduit 160 is open and completes a path from the bottom of outlet manifold 140 through the pH sensor cuvette 166 to the top of inlet manifold 138. When the valve rods are moved to the left, that path is closed; and a supply path through conduits 30 and 160 to the top of inlet manifold 138 and a discharge path from the lower portion of conduit 140 to discharge conduit 34 are opened.

Similarly, valve 170 has two positions, a first position in which valve rod 190-5 compresses tube 26 against backup surface 192-5a and opens the connector conduit 172 to connect the lower ends of the two manifolds together; and a second position in which the rod compresses junction conduit 172 against backup surface 192-5b, closing the junction conduit and opening conduit 26, permitting flow of liquid from the outlet manifold 140 to the pH cuvette 166.

Additional details of the construction of a portion of valve 22, which is typical of the three valves, is shown in FIG. 12. As indicated in that figure, there is a valve housing 200 in which are formed slots 202 for receiving the tubing sections in releasably secured manner so that the tubing may be removed easily for ready replacement. The manifold sections 138, 140 preferably are permanently connected to the peristaltic tubing sections and the entire subassembly may be readily replaced as a unit. The sections are plugged into the pH electrode cuvette 166 and that cuvette is steam sterilizable as is the cooperating pH electrode 196, which in a particular embodiment is a combination pH electrode.

A system flow and control diagram is indicated in FIG. 13. As there indicated, the chamber units 50 are connected to the inlet and outlet manifolds 138, 140, respectively, positive displacement peristaltic pumps 16 being connected to the inlet lines 74 of the sample chamber units. Supply line 30 is connected to nutrient supply container 32 and discharge line 34 is connected to collection container 36. pH sensor 20 monitors the hydrogen ion concentration in the liquid leaving the discharge manifold 140 and its output signal is applied over cable 210 to controller 212 which has output 214 connected to carbon dioxide controller 216 and output 218 connected to nitrogen controller 220. Oxygen sensor 40 in the gaseous environment in incubator chamber 10 provides an output signal through collector 222 to control nitrogen controller 220 (line 224) and oxygen controller 226 (line 228).

Nutrient media is supplied to the system from source 32 through valve 22 which, during system operation, is under control of carbon dioxide sensor 42 which is arranged normally to monitor the carbon dioxide in housing 10. A source of calibrated carbon dioxide 46 is connected to sensor 42 via valve 48 as periodic calibration of sensing unit 42 is desirable. Accordingly, valve 48 is periodically operated, for example one minute for each hour of system operation, and the flow of calibrated carbon dioxide from source 46 past sensor 42 provides a calibration or reference signal. This calibration signal is stored and through the remainder of the operating cycle, valve 48 is positioned so that sensor 42 monitors the carbon dioxide content in the incubator, the output of sensor unit 42 being applied to controller 230 and the resulting output signal over line 232 controlling valve 22.

Another embodiment is illustrated in FIGS. 14–16. In this embodiment components that contact the nutrient media are mounted on a carriage or support assembly 250 that is removable from incubator 10. That support assembly, as indicated in FIGS. 14–16, includes a rectangular frame structure that has a base member 252, side walls 254, 256 and top wall 258. Extending between side walls 254, 256 are four sets of rod elements 12', 14' that are supported for rotation in suitable bearing structures (not shown) mounted on side wall 254, 256. Each rod element 12 extends through wall 256 and has a sprocket 260 secured to it. A chain 262 is trained about sprockets 260 so that the four support rods 12' may be driven simultaneously. A spring loaded coupling drive member 264 extends laterally outwards from the lower and forward one of sprockets 260.

Each pair of support rods 12', 14' is arranged to receive five replaceable, sterilizable, cell growth assemblies 50' which may be of the type as shown in FIGS. 3–5 or as shown in our co-pending application Ser. No. 499,515, filed Aug. 22, 1974 and entitled "Cell Culture" for example. A first set of five peristaltic pump structures diagrammatically indicated at 16' is mounted on framework 266 for used with the upper ten cell culture chambers 50', while a second set of five peristaltic pump structures 16' for use with the lower 10 cell culture chambers is mounted on base 252. Forward of frame 266 is mounted a first manifold assembly 270 as supported by brackets 272, while a second manifold structure 276 is secured to base 252 by brackets 278. Each manifold structure has ten pairs of couplings 280 in communication with manifold tubes 138', 140' mounted within manifold structures 270, 274 and to which inlet and outlet conduit tubing 74', 76' from corresponding culture chamber assemblies 50' may be detachably secured. Each manifold assembly includes valves 162', 170' and each is connected to common pH sensor 20' and common valve 22'.

Each peristaltic pump structure 16' is arranged so that two inlet conduits 74' may be trained about its cage for servicing two culture chambers 52'. The removable carriage 250 also includes a common drive for the 10 pumps 16'. Each pump cage has a sprocket 290 and a common chain 292 links the five sprockets of each set together. The shaft 294 of one cage extends rearwardly through a support bearing 296 and carries a sprocket 298 and a rearwardly projecting coupling 300. A chain 302, trained over sprocket 298, extends down over sprocket 304 that is connected to auxiliary drive shaft 306 which is arranged for driving the cages of the lower set of five pumps 16' through drive mechanism 308. PH sensor cuvette 166' and electrode 196' are mounted on side wall 256 of the carriage 250. Casters 310 are secured to the base 252 of the support assembly 250 and enable that assembly, with culture assemblies 50' in position to be easily rolled into and out of the incubator 10.

One side of incubator 10, as indicated in FIG. 14, is arranged to be closed by door 312. A transparent auxiliary door 314 permits viewing of the interior of the incubator 10' without disturbing the controlled environment therein. Valve 22' is mounted in the face of one side wall of the incubator and conduit sections 24', 30', 34' and 160' are manually detachable from recesses 202' in the housing 200' of valve 22'. Cable 210' from pH sensor 20' is also detachably secured in recess 202'' adjacent the housing 200' of valve 22'. Peristaltic pump drive 320 is mounted on the rear of incubator 10' and has a shaft 322 that extends through the wall of incubator for connection via coupling 324 to coupling 300. A similar drive 326 is mounted on a side wall of the incubator and has shaft 328 and coupling 330 arranged for engagement with chamber drive coupling 264. Other appropriate passages e.g. port 44' (not shown) enable the introduction of gases into the interior of the incubator to provide the desired controlled environment and the transmission of signals to the controller. Support carriage 250 is removable as a unit from incubator 10 and facilitates sterilization as a unit of components that contact nutrient media, such as the chamber assemblies 50', the pH sensor 20' and the collection bottle 36'. The removable carriage also facilitates mounting of cell culture chambers on the supports, servicing, and innoculation of the cell culture chambers 52'.

In operation with either embodiment, the chamber units 50 are positioned with their reel flanges on support rods 12, 14 in the incubator chamber, the inlet lines 74 trained about the peristaltic pump cages 90 and secured by positioning the tube locks 80 in notches 84; and the inlet and outlet conduits 74, 76 are operatively connected to manifolds 138, 140, for example by friction coupling or with connectors 100.

The manifolds 138, 140 are filled with the liquid nutrient from supply 32 (either prior or subsequent to connecting the culture chambers) by operating valve 22 to close coupling line 160, valve 162 to open the vent passage 176, and valve 170 to connect the lower ends of the two manifold chambers together. The nutrient then flows from supply 32 under gravity into the two manifold chambers and fills them, any air and excess nutrient being vented through line 176 to the collection bottle 36.

The cells or tissues may be introduced into the chambers 52 through one of the terminal openings together with an amount of nutrient media, or a cell suspension may be injected through the wall of the chamber 52 into the nutrient media by means of a syringe. The puncture is sealed spontaneously by the resilient sheet chamber material upon withdrawal of the needle. During the filling of the spiral chambers with nutrient material, the reels 70 may be drive through about 360° rotation at a low rate of speed to assist in displacing gases, distributing cells, and improving contact of the nutrient material with the cells. After the cells are introduced and distributed through the spiral chambers, the system is maintained static for an interval to facilitate the attachment of cells to the chemically etched (roughened) inner walls of the chambers.

While cells are being grown in the chambers 52, the incubator 10 is held at desired conditions of humidity and temperature, typically 37° C, the nutrient media is circulated by pumps 16, the pH of the circulating nutrient media and the partial pressure of oxygen in the gas phase are monitored, and the partial pressure of the carbon dioxide in the gas phase is adjusted to maintain the pH of the liquid media at a selected value, typically about 7. The length of chambers 52 assure that liquid in the circulation system and the gas phase in the enclosure of the incubator 10 are in gas equilibrium through the permeable walls of the chambers 52. The output of pH sensor 20 controls the carbon dioxide and nitrogen controllers 216 and 220, additional carbon dioxide being admitted when pH rises and a reduced amount of carbon dioxide being admitted when the pH fails. Oxygen and nitrogen are admitted continuously at low and controlled flow rates to maintain the desired partial pressure of oxygen in the incubator 10.

After an interval of time, the accumulation of components, such as lactic acid which is produced by many growing cells, in the circulating nutrient media may make it impossible to maintain the desired pH by reducing the amount of carbon dioxide in the chamber. When the amount of carbon dioxide in the chamber drops below a selected value, the output of controller 230 shifts valve 22 so that at least a portion of the circulating nutrient media is transferred through discharge line 34 and replaced by fresh media uncontaminated by the products of cell metabolism through supply conduit 30.

While a particular embodiment of the invention has been shown and described, various modifications thereof will be apparent to those skilled in the art, and therefore it is not intended that the invention be limited to the disclosed embodiment or to details thereof and departures may be made therefrom within the spirit and scope of the invention as defined in the claims.

What is claimed is:

1. A cell culture system comprising a housing, a cell culture chamber support assembly in said housing and removable from said housing, a cell culture chamber on said support assembly, said cell culture chamber being a replaceable, sterilizable elongated tubular member of gas permeable, liquid impermeable material and having an inner surface to which cells are attachable and an outer surface exposed to the gaseous environment in said housing, said tubular member being disposed in a plurality of layers in spiral relation, spacer structure between adjacent layers of said spiral chamber maintaining said adjacent layers spaced from one another to permit gas to contact external surfaces of said spiral chamber over substantially its entire length, circulation path structure on said support assembly including supply and return conduits connected to said cell culture chamber so that an elongated spiral flow path between said supply and return conduits is provided by said chamber, pump means on said support assembly for circulating nutrient media along said circulation path and across said inner surface of said cell culture chamber, a detachable drive coupling on said support assembly for connecting said pump means to an external power source, a valve and a pH sensor in said circulation path, a carbon dioxide sensor in said housing, a first control responsive to said pH sensor for controlling the introduction of carbon dioxide to said housing, and a second control responsive to said carbon dioxide sensor for operating said valve to discard at least a portion of the nutrient media circulating in said circulation path and replace such discarded portion with fresh nutrient media.

2. The system as claimed in claim 1 and further including coupling structure connected to said circulation path, said coupling structure including a first coupling portion that includes a body member that supports a projecting rigid conduit, said rigid conduit having an orifice and a puncturing tip adjacent said orifice, a seal member of elastomeric material, said puncturing tip being imbedded in said seal member, and a guide member secured to said seal member and extending parallel to said projecting rigid conduit for sliding movement relative to said body member so that said conduit orifice may be opened by sliding said seal member along said rigid conduit as guided by said guide member to expose the tip of said rigid conduit, said orifice being reclosed by sliding said seal member in the opposite direction away from said body member to reposition said orifice of said rigid conduit in said seal member, and a second coupling portion that includes a conduit of elastomeric material and a receptacle for receiving said seal member of said first coupling in position so that movement of said body member towards said sealing member forces the orifice of said rigid conduit through said seal member and into the cooperating elastomeric conduit to establish a flow path between said cooperating conduit and said rigid conduit.

3. The system as claimed in claim 1 wherein said pulp means includes peristaltic pump structure that has a rotatable cage, on said support assembly and said supply conduit is of flexible tubing and includes tapered tube lock structure disposed within the tubing and defining a flow path past the tube lock structure within said tubing for cooperation with said peristaltic pump structure so that a length of said tubing may be maintained in tension when trained about said cage of said peristaltic pump.

4. The systme as claimed in claim 3 and further including coupling structure connected to said supply and return conduits, said coupling structure includes a first coupling portion that includes a body member that supports a projecting rigid conduit, said rigid conduit having an orifice and a puncturing tip adjacent said orifice, a seal member of elastomeric material, said puncturing tip beng imbedded in said seal member, and a guide member secured to said seal member and extending parallel to said projecting rigid conduit for sliding movement relative to said body member so that said conduit orifice may be opend by sliding said seal member along said rigid conduit as guided by said guide member to expose the tip of said rigid conduit, said orifice being reclosed by sliding said seal member in the opposite direction away from said body member to reposition said orifice of said rigid conduit in said seal member, and a second coupling portion that includes a conduit of elastomeric material and a receptacle for receiving said seal member of said first coupling in position so that movement of said body member towards said sealing member forces the orifice of said rigid conduit through said seal member and into the cooperatng elastomeric conduit to establish a flow path between said cooperating conduit and said rigid conduit.

5. The cell culture system as claimed in claim 1 wherein said pH sensor is also mounted on and removable from said housing as a unit with said support assembly.

6. A cell culture assembly for use with an incubator housing, said assembly comprising a carriage adapted to be inserted into said incubator housing, support on said carriage for a plurality of cell culture chambers, a plurality of cell culture chambers on said support, each said chamber including a replaceable, sterilizable elongated tubular member of gas permeable liquid impermeable material, having an inner surface to which cells are attachable, each said tubular member being wound in a spiral and defining an elongated spiral flow path, supply manifold structure and return manifold structure on said carriage, coupling structure for detachably connecting said cell culture chambers on said support to said supply and return manifold structures, pump means on said carriage for circulating nutrient media from said supply manifold structure through said cell culture chambers on said support for flow along the spiral flow paths of said chambers and return to said return manifold structure, a detachable drive coupling on said carriage for connecting said pump means to an external power source, and sensor structure on said carriage for sensing media in said circulation path and providing an output signal representative thereof, said carriage being removable as a unit from said incubator housing for sterilization of components thereon.

7. The assembly as claimed in claim 6 wherein each said chamber further includes elongated, flexible, supply and return conduit tubes adapted for detachable connection to said manifold structure to introduce culture media for flow through said chamber, and to receive culture media from said chamber.

8. The assembly as claimed in claim 7 wherein each said chamber is made of a sheet of plastic material, one surface of which is rougher than the other surface, said sheet being folded and sealed to provide a steam sterilizable chamber with said one surface forming the inner surface of said chamber and providing a surface to which cells to be cultured adhere.

9. The assembly as claimed in claim 6 wherein said pump means includes positive displacement pump structure for pumping culture media through said supply and return conduits and said sensor is a pH sensor connected to said manifold structure for sensing the pH of circulating culture media.

10. A cell culture system comprising an incubator housing, a carriage in said housing and removable from said housing, cell culture chamber support structure on said carriage, a plurality of cell culture chambers on said support structure, each said cell culture chamber being a replaceable, sterilizable, elongated tubular member of gas permeable liquid impermeable material having an inner surface to which cells are attachable and an outer surface exposed to the gaseous environment in said housing, circulation path structure on said carriage including flexible inlet and outlet conduits, pump means on said carriage and coupled to each inlet conduit for circulating nutrient media from said supply manifold along a circulation path through each said inlet conduit, its associated cell culture chamber, and its associated outlet conduit to said return manifold, a detachable drive coupling on said carriage for connecting said pump means to an external power source, a valve and a first sensor in said circulation path structure, a second sensor in said housing, a first control responsive to said first sensor for controlling the introduction of gas to said housing, and a second control responsive to said second sensor for operating said valve to discard at least a portion of the nutrient media circulating in said circulation path and replace such discarded portion with fresh nutrient media.

11. The system as claimed in claim 10 wherein said first sensor is a pH sensor and is mounted on and is removable from said housing as a unit with said carriage.

12. The assembly as claimed in claim 6 wherein each said chamber has flexible conduit means for connection to said manifold structure and said pump means includes peristaltic pump structure in pumping engagement with each said flexible conduit means.

* * * * *